(12) United States Patent
Nazarifar et al.

(10) Patent No.: US 12,318,532 B2
(45) Date of Patent: Jun. 3, 2025

(54) SYSTEM LEVEL FLUIDICS AND CONTROLS

(71) Applicant: Johnson & Johnson Surgical Vision, Inc., Irvine, CA (US)

(72) Inventors: Nader Nazarifar, Laguna Niguel, CA (US); Justin Lin, Tustin, CA (US); Deep Mehta, Irvine, CA (US)

(73) Assignee: Johnson & Johnson Surgical Vision, Inc., Irvine, CA (US)

(*) Notice: Subject to any disclaimer, the term of this patent is extended or adjusted under 35 U.S.C. 154(b) by 120 days.

(21) Appl. No.: 17/124,486

(22) Filed: Dec. 16, 2020

(65) Prior Publication Data

US 2021/0178036 A1 Jun. 17, 2021

Related U.S. Application Data

(60) Provisional application No. 62/949,436, filed on Dec. 17, 2019.

(51) Int. Cl.
  *A61M 1/00* (2006.01)
(52) U.S. Cl.
  CPC ............ *A61M 1/802* (2021.05); *A61M 1/774* (2021.05); *A61M 2205/123* (2013.01); *A61M 2205/128* (2013.01); *A61M 2210/0612* (2013.01)
(58) Field of Classification Search
  CPC ................. A61M 1/802; A61M 1/774; A61M 2205/123; A61M 2205/128; A61M 2210/0612
  See application file for complete search history.

(56) References Cited

U.S. PATENT DOCUMENTS

| | | | | |
|---|---|---|---|---|
| 5,195,960 | A * | 3/1993 | Hossain | F04B 43/1253 417/477.2 |
| 2002/0004657 | A1* | 1/2002 | Morgan | A61M 1/742 604/35 |
| 2006/0025727 | A1 | 2/2006 | Boehringer et al. | |
| 2007/0278155 | A1 | 12/2007 | Lo et al. | |
| 2009/0281485 | A1* | 11/2009 | Baker | A61B 10/0045 604/35 |
| 2015/0094697 | A1* | 4/2015 | Rinderknecht | A61M 5/14276 156/293 |
| 2019/0183679 | A1 | 6/2019 | Sawicz | |
| 2019/0365567 | A1* | 12/2019 | Balkenbush | A61F 9/00745 |
| 2020/0011321 | A1* | 1/2020 | Bannwart | A61M 3/0201 |
| 2020/0360185 | A1* | 11/2020 | Carter | A61F 9/00754 |
| 2021/0290836 | A1* | 9/2021 | Köppel | A61M 1/774 |

FOREIGN PATENT DOCUMENTS

| | | | |
|---|---|---|---|
| CA | 2003184 A1 | 4/1990 | |
| EP | 3318291 A1 | 5/2018 | |

OTHER PUBLICATIONS

"How Diaphragm Pumps Work." Verder Liquids. Accessed 2023. <https://www.verderliquids.com/us/en/pump-technologies/what-is-a-diaphragm-pump> (Year: 2023).*

* cited by examiner

*Primary Examiner* — Scott J Medway (57) ABSTRACT

A pressure and vacuum pump including at least two diaphragm pump heads for providing vacuum and pressure simultaneously. The dual function pump reduces number of required pumps, is traditionally quieter, and enables the system to run at a lower duty cycle. A drive in the pump housing causes a connecting rod to oscillate a diaphragm to move up and down thereby causing air to be either drawn into an inlet or forced out via an exhaust.

12 Claims, 8 Drawing Sheets

SYSTEM LEVEL FLUIDICS AND CONTROLS

CROSS-REFERENCE TO RELATED APPLICATIONS

This application claims the benefit under 35 U.S.C. § 119(e) of U.S. Provisional Patent Application No. 62/949,436, filed Dec. 17, 2019, which is incorporated herein by reference in its entirety.

BACKGROUND OF THE INVENTION

Field of Technology

The present invention relates generally to pressure and vacuum pumps for phacoemulsification surgery, and, more specifically, to a pressure and vacuum pump including at least two diaphragm pump heads for providing vacuum and pressure simultaneously.

Description of the Background

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil and within a capsular bag, the capsular bag being a thin, relatively delicate structure which separates the eye into anterior and posterior chambers.

With age, clouding of the lens or cataracts is fairly common. Cataracts may form in the hard central nucleus of the lens, in the softer peripheral cortical portion of the lens, or at the back of the lens near the capsular bag. Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humor in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms may be used in phacoemulsification and other treatment systems for the eyes, aspiration flow systems can generally be classified in two categories: 1) volumetric based aspiration flow systems using positive displacement pumps (e.g. peristaltic); and 2) vacuum-based aspiration systems using a vacuum source, typically applied to the aspiration flow through an air-liquid interface within a reservoir (e.g. Venturi). Both systems may be incorporated into one treatment system and/or cassette. Cassette ("pack") systems can be used to couple peristaltic pump drive rotors and/or vacuum systems of the surgical consoles to an eye treatment handpiece, with the flow network conduit of the cassette being disposable to avoid cross-contamination between different patients.

To mitigate such occurrences, staff operating a system typically begin each procedure with a fresh cassette and irrigation source prior to each case, and monitor the fluid visually throughout surgery. However, conventional configurations do not efficiently provide for easily exchangeable cassettes which can optimally perform certain intended functions. As such, improvements are needed in the art to address these issues.

SUMMARY

The present invention discloses system for distributing fluid in a phacoemulsification surgical system, comprising, a cassette for use with a surgical console having a set of channels suitable for fluid movement, a diaphragm pump, further comprising an inlet, an exhaust, at least two pump heads, and a connecting rod configured to oscillate causing the diaphragm to move up and down. Further, in response to oscillation of the connecting rod, air may be drawn into the inlet and forced out via the exhaust. The at least two pump heads may be diaphragm pump heads and may provide a vacuum fluidly available within the cassette and may provide a positive pressure fluidly available within the cassette or to a pressure reservoir. Further, each of the pump heads may operate simultaneously.

DESCRIPTION OF THE DRAWINGS

The accompanying drawings are included to provide a further understanding of the invention and are incorporated in and constitute a part of this specification. The drawings illustrate disclosed embodiments and/or aspects and, together with the description, serve to explain the principles of the invention, the scope of which is determined by the claims.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

A surgical cassette, also referred to as a medical pack, a fluidic cassette, or simply, a cassette, is used to facilitate irrigation and aspiration during surgical procedures, such as phacoemulsification surgery. The surgical cassette may be inserted and mounted to a surgical console and become part of an overall phacoemulsification surgery system. The surgical cassette may perform a myriad of functions, such as effluent material collection, tube pressure sensing, and control the flow of fluid through tubing encased within the cassette and between a surgical handpiece and a surgical console.

A surgical cassette typically comprises a front plate and a back plate, and may also include a gasket at least partially there between. Other configurations of the cassette are contemplated with the present invention. Molded within either/or the front plate and the back plate may be pathways for fluid flow and/or for tubing to be inserted thereby creating desired pathways for the tubing around the gasket. In an embodiment where there is a gasket, the gasket may comprise one or more valves and one or more sensors to promote fluid flow through the tubing along the desired pathways. In another embodiment, a surgical cassette may have no tubing and/or gasket. In an embodiment where there is no gasket, any valves known in the art may be used, e.g., a rotary valve.

Surgical cassettes may utilize different types of sensors to monitor pressure, vacuum, and/or flow of certain fluid lines during the surgical process. Other single use cassettes may use a low-cost pressure diaphragm on the cassette with a console mounted Linear Variable Differential Transformer (LVDT) to measure the deflection of the pressure diaphragm with either a low rate spring pushing the LVDT against the surface of the pressure diaphragm or a magnet coupling the LVDT to the surface of the diaphragm, or a combination of both a spring and magnet. The spring force and/or friction force associated with movement of the LVDT sensing element reduces the accuracy and repeatability of this type system. Other systems may use laser triangulation displacement sensors to measure the deflection of a pressure diaphragm. In addition, other systems may use a ferromagnetic element in the cassette which couples to a magnetic element in the console, which may be coupled with a strain gauge.

Figure 1A:
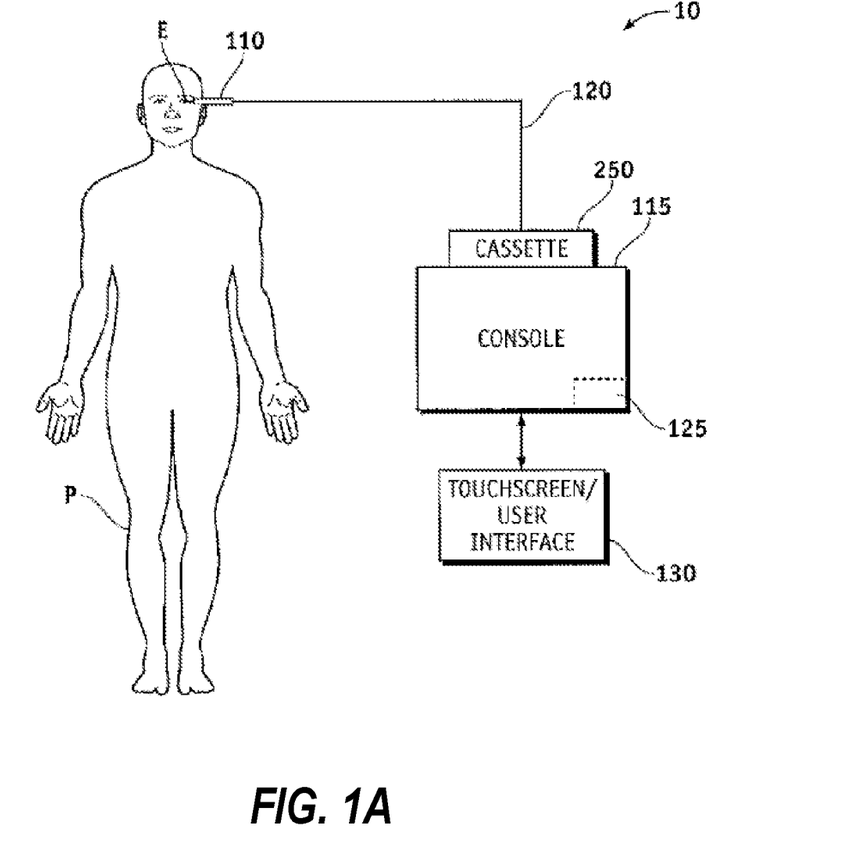
FIG. 1A is a schematic illustrating an eye treatment system in which a cassette is coupled to an eye treatment probe with an eye treatment console under one embodiment.

Referring now to FIG. 1A, a system 10 for treating an eye E of a patient P generally includes an eye treatment probe handpiece 110 coupled with a console 115 by a cassette 250. Handpiece 110 generally includes a handle for manually manipulating and supporting an insertable probe tip. The probe tip has a distal end which is insertable into the eye, with one or more lumens in the probe tip allowing irrigation fluid to flow from console 115 and/or cassette 250 into the eye. Aspiration fluid may also be withdrawn through a lumen of the probe tip, with console 115 and cassette 250 generally including a vacuum aspiration source, a positive displacement aspiration pump, or both to help withdraw and control a flow of surgical fluids into and out of eye E. As the surgical fluids may include biological materials that should not be transferred between patients, cassette 250 will often comprise a sterilizable (or alternatively, disposable) structure, with the surgical fluids being transmitted through flexible and/or rigid conduits 120 of cassette 250 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an irrigation/aspiration (I/A) and/or vitrectomy handpiece. Also, the ultrasonic transmitter may be replaced by other means for emulsifying a lens, such as a high energy laser beam. The ultrasound energy from handpiece 110 helps to fragment the tissue of the lens, which can then be drawn into a port of the tip by aspiration flow. So as to balance the volume of material removed by the aspiration flow, an irrigation flow through handpiece 110 (or a separate probe structure) may also be provided, with both the aspiration and irrigation flows being controlled by console 115.

To avoid cross-contamination between patients without incurring excessive expenditures for each procedure, cassette 250 and its flexible conduits 120 may be disposable. However, the flexible conduit or tubing may be disposable, with the cassette body and/or other structures of the cassette being sterilizable. Cassette 250 may be configured to interface with reusable components of console 115, including, but not limited to, peristaltic pump rollers, a Venturi or other vacuum source, a controller 125, and/or the like.

Console 115 may include controller 125, which may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader, or the code may be transmitted to controller 125 by a network connection such as an internet, an intranet, an ethernet, a wireless network, or the like. Along with programming code, controller 125 may include stored data for implementing the methods described herein, and may generate and/or store data that records parameters corresponding to the treatment of one or more patients.

Figure 1B:
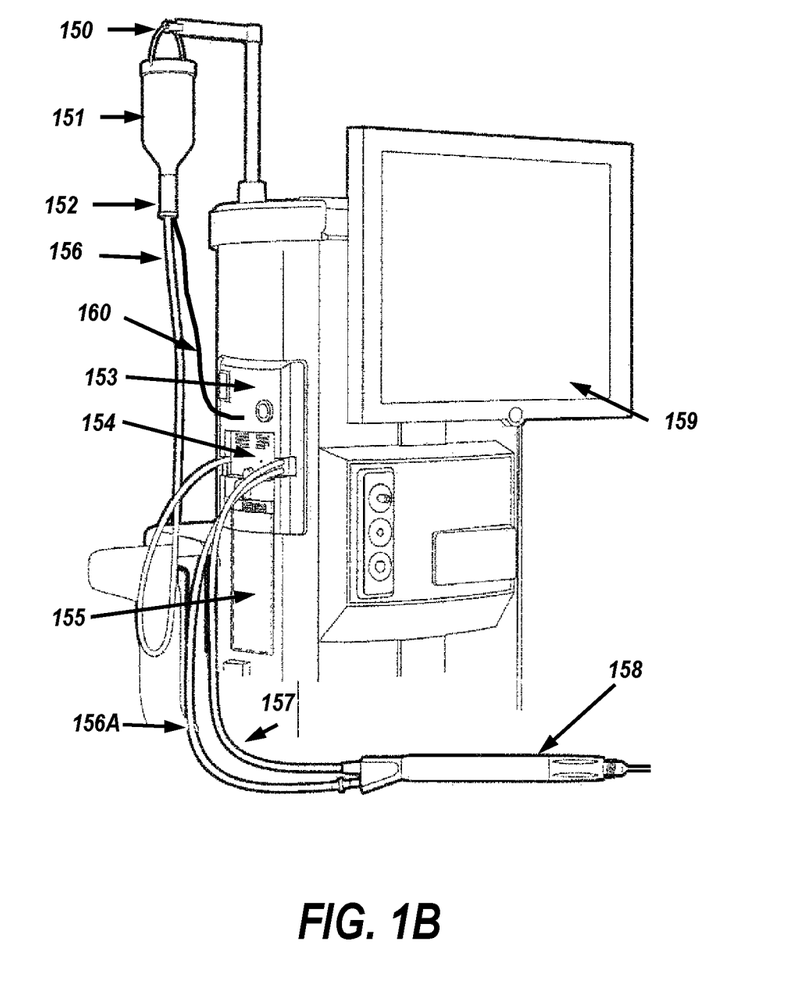
FIG. 1B is a schematic illustrating a surgical eye treatment console under another exemplary embodiment.

Referring now to FIG. 1B, a simplified surgical console is illustrated, where a fluid path may be demonstrated under an exemplary embodiment. In this example, an irrigation source 151 may be configured as a bottle or bag hanging from an IV pole hanger 150. It is understood by those skilled in the art that, while an integrated IV pole is illustrated, other configurations, utilizing standalone/static IV poles, pressurized infusion sources, and/or other suitable configurations, are contemplated by the present disclosure.

An exemplary irrigation path for fluid may be realized via tubing cassette 154 having cassette tubing interface or receptable 153, which receives fluid from irrigation source 151 via drip chamber 152. Irrigation line 156A and aspiration line 157 are coupled to handpiece 158. Irrigation fluid may flow from drip chamber 152 through the irrigation tubing into tubing cassette 154. Irrigation fluid may then flow from the tubing cassette through handpiece irrigation line 156A which may be coupled to an irrigation port on handpiece 158. Aspirated fluid may flow from the eye through the handpiece aspiration line 157 back to tubing cassette 154 and into a waste collection bag 155. A touch screen display 159 may be provided to display system operation conditions and parameters, and may include a user interface (e.g., touch screen, keyboard, track ball, mouse, etc.—see controller 125 of FIG. 1A) for entering data and/or instructions to the system of FIG. 1B.

Figure 2:
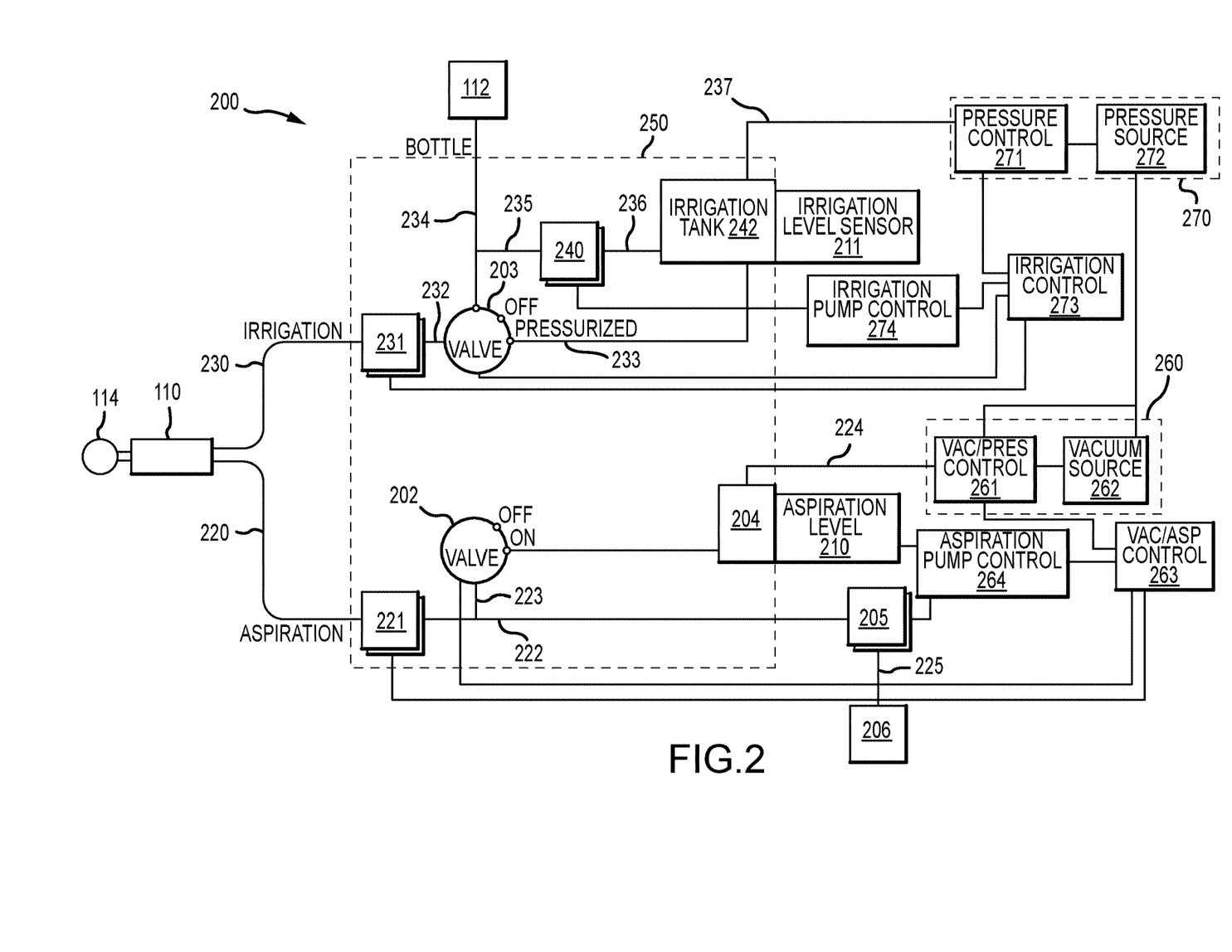
FIG. 2 is a functional block diagram of an exemplary cassette system for an eye treatment system under one embodiment.

Referring to FIG. 2, an exemplary cassette system showing some of the components and interfaces that may be employed in a phaco system, such as ones illustrated in FIGS. 1A-B. Handpiece 110 may be connected to (or coupled with) the input side of sensor 221, typically by fluid pathways such as fluid pathway 220. Sensor 221 may be a pressure, flow, or a vacuum sensor that measures pressure, flow or vacuum, respectively. In a preferred embodiment, sensor 221 is a pressure sensor. The output side of sensor 221 is connected to valve 202 and also connected to pump 205 within cassette 250 via fluid pathway 222. Valve 202 may be any known valve in the art, e.g., flow selector valve, rotary valve, etc. Valve 202 may also be coupled with pump 205. The exemplary embodiment may configure valve 202 to interface between handpiece 110, vacuum tank 204, pump 205, which may be a peristaltic pump but may be another type of pump, and collection 206. In this configuration, the system may operate valve 202 to connect handpiece 110 with vacuum tank 204 based on signals received from console 115 resulting from the surgeon's input to user interface 130. In an embodiment, the handpiece 110 is always connected to pump 205 and valve 202 and may be toggled to connect or disconnect the handpiece 110 to the tank 204. As discussed herein in greater detail, an aspiration level sensor 210 may be communicatively coupled to vacuum tank 204.

The valve 202 illustrated in FIG. 2 may provide a connection between vacuum tank 204 and fluid pathway 222. The exemplary embodiment is not limited to one flow and may be realized using two valves each having at least two output ports, possibly connected together to provide the functionality described herein. For example, a pair of two valves may be configured in a daisy chain arrangement, where the output port of a first valve is directly connected to the input port of a second valve. Console 115 may operate both valves together to provide three different flow configurations. For example, using two valves, valve one and valve two, valve one may use output port one, which is the supply for valve two. Valve two may connect to one of two ports providing two separate paths. When valve one connects its input port to its second output port rather than the output port that directs flow to the second valve, a third path is provided. It is also envisioned that valve 202 may be or comprise one or more pinch valves. The one or more pinch valves may be located along fluid pathway 220, 222 and/or 223, or any other fluid pathway as discussed herein.

Console 115 may also comprise vacuum pressure center 260 which may provide a vacuum through fluid pathway 224 to vacuum tank 204. The vacuum provided through fluid pathway 224 may be regulated by control module 261 based on signals received from aspiration control module 263 which may result from the surgeon's input to user interface 130 and/or based on other signals received from vacuum pressure sensor 221. Aspiration control module 263 may also control pump control 264 and allow for operation of pump 205 for the movement of fluid from both the handpiece 110 and the vacuum tank 204 to collector 206 via pathway 225.

In the configuration shown, vacuum pressure center 260 includes a vacuum source 262, such as a venturi pump and an optional control module 261 (and valve (not shown)), but other configurations are possible. In this arrangement, vacuum pressure center 260 may operate to remove air from the top of vacuum tank 204 and deliver the air to atmosphere (not shown). Removal of air from vacuum tank 204 in this manner may reduce the pressure within the tank, which may reduce the pressure in the attached fluid pathway 220, to a level less than the pressure within eye 114. A lower reservoir pressure connected through valve 202 may cause fluid to move from the eye, thereby providing aspiration.

Thus, while a single valve 202 (such as for example, a flow selector valve) is illustrated in FIG. 2 associated with aspiration, it is to be understood that this illustration represents a valve arrangement, including one or more valves performing the functionality described herein, and is not limited to a single device or a single valve. In the exemplary vacuum pressure sensor 221, a strain gauge or other suitable component may communicate or signal information to console 115 to provide an amount of vacuum sensed in the handpiece fluid pathway 220. Console 115 may determine the actual amount of vacuum present based on the communicated information.

Sensor 221 monitors the pressure of fluid flowing into and out of the line and can be used to determine when fluid flow should be reversed, such as encountering a certain pressure level (e.g. in the presence of an occlusion), and based on values obtained from the sensor 221, the system may control selector valve 202 and the pumps illustrated. It is to be understood that while components presented in FIG. 2 and other drawings of the present application are not shown connected to other system components, such as console 115, they are in fact connected for the purpose of monitoring and control of the components illustrated.

With respect to sensor 221, emergency conditions such as a dramatic drop or rise in pressure may result in a type of fail-safe operation. The exemplary embodiment employs sensor 221 to monitor the flow conditions and provide signals representing flow conditions to the system such as via console 115 for the purpose of controlling components shown including but not limited to selector valve 202 and the pumps shown. The fluid pathways or flow segments of surgical cassette system 200 may include the fluid connections, for example flexible tubing, between each component represented with solid lines in FIG. 2. In an embodiment, the fluid connections may include molded fluid channels.

Handpiece 110 may be connected to (or coupled with) the output side of irrigation sensor 231, typically by fluid pathways such as fluid pathway 230. Sensor 231 may be a pressure, flow, or a vacuum sensor that measures pressure, flow or vacuum, respectively. In a preferred embodiment, sensor 231 is a pressure sensor. The input side of irrigation sensor 231 may be connected to valve 203 within cassette 250 via fluid pathway 232. Valve 203 may be any known valve in the art, e.g., flow selector valve, rotary valve, etc. The exemplary embodiment may configure valve 203 to interface between handpiece 110, irrigation tank 242, pump 240, which may be a peristaltic pump but may be another type of pump, and irrigation fluid source 112. In this configuration, the system may operate valve 203 to connect handpiece 110 with gravity feed or pressurized irrigation based on signals received from console 115 resulting from the surgeon's input to user interface 130.

The valve 203 illustrated in FIG. 2 may provide a connection between irrigation tank 242, irrigation fluid source 112, and fluid pathway 232. The exemplary embodiment is not limited to one valve and may be realized using two valves each having at least two output ports, possibly connected together to provide the functionality described herein. For example, a pair of two valves may be configured in a daisy chain arrangement, where the output port of a first valve is directly connected to the input port of a second valve. Console 115 may operate both valves together to provide three different flow configurations. For example, using two valves, valve one and valve two, valve one may use output port one, which is the supply for valve two. Valve two may connect to one of two ports providing two separate paths. When valve one connects its input port to its second output port rather than the output port that directs flow to the second valve, a third path is provided. It is also envisioned that valve 203 may be or comprise one or more pinch valves. The one or more pinch valves may be located along fluid pathway 230, 232, 233, 234 and/or 235, or any other fluid pathway as discussed herein.

Console 115 may also comprise irrigation pressure center 270 which may provide a positive pressure through fluid pathway 237 to irrigation tank 242. Irrigation pressure center may include pressure control 271 and pressure source 272. The pressure provided through fluid pathway 237 may be regulated by control module 271 based on signals received from irrigation control module 273 which may result from the surgeon's input to user interface 130 and/or based on other signals received from vacuum pressure sensor 231. Irrigation control module 273 may also control irrigation pump control 274 and allow for operation of pump 240 for the movement of fluid from irrigation fluid source 112 to collector irrigation tank 242 via pathway 236. In addition, an irrigation level sensor 211 may be communicatively coupled with the irrigation tank 242.

While a single valve 203 is illustrated in FIG. 2 associated with irrigation, it is to be understood that this illustration represents a valve arrangement, including one or more valves performing the functionality described herein, and is not limited to a single device or a single valve. In the exemplary irrigation sensor 231, a strain gauge or other suitable component may communicate or signal information to console 115 to provide an amount of pressure sensed in the handpiece fluid pathway 230. In another embodiment, depending upon the sensor used, an amount of vacuum or flow may be sensed in the handpiece fluid pathway 230 and communicated to console 115. Console 115 may determine the actual amount of pressure present based on the communicated information.

Figure 3:
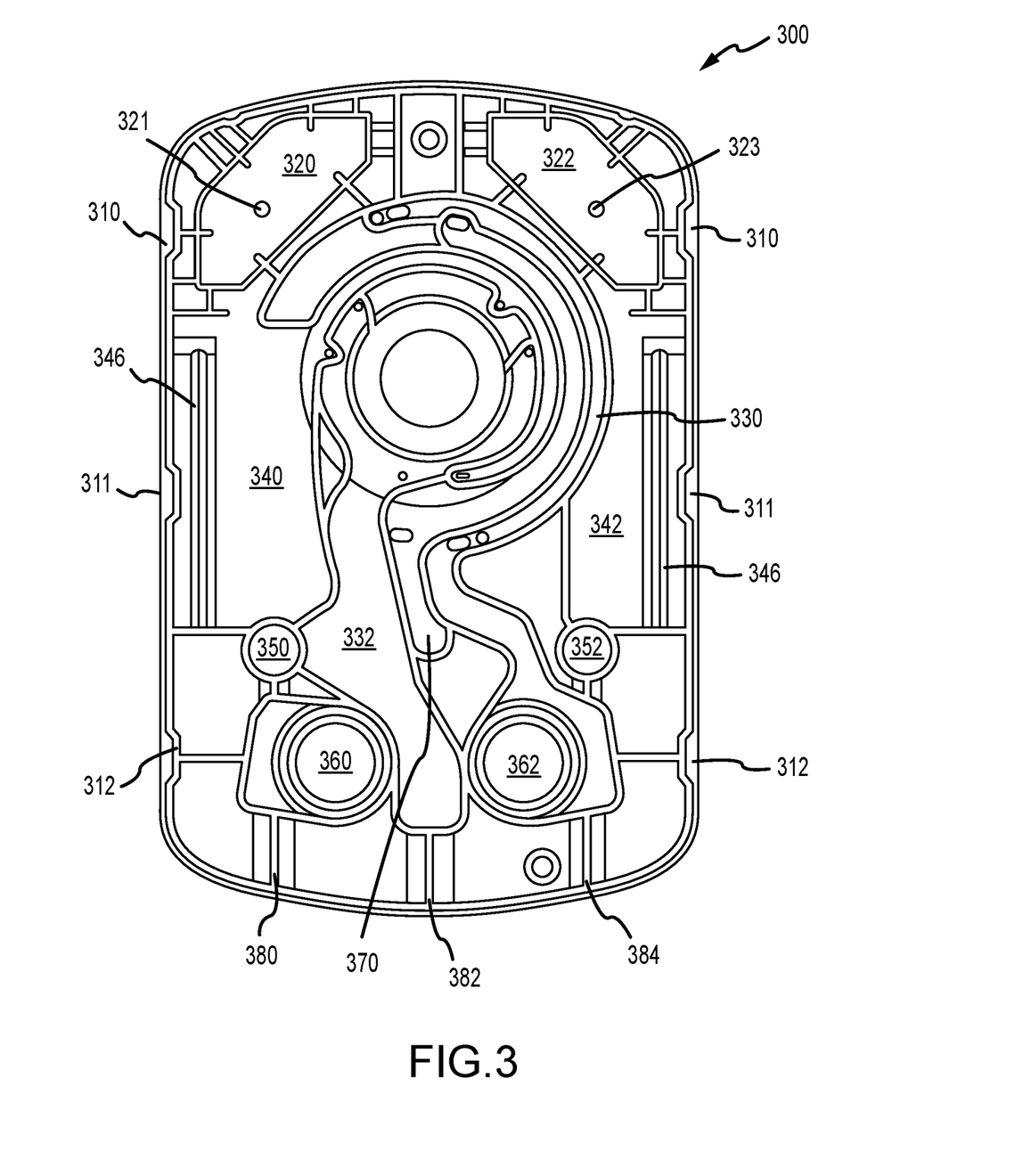
FIG. 3 is a schematic illustrating a cassette under another exemplary embodiment.

FIG. 3 illustrates an exemplary surgical cassette showing some of the features which may be employed in a phaco system. Cassette 300 may include a series of detents, also referred to as notches or catch surfaces, along its outer edge for receiving at least a portion of a retention device which may be associated with a surgical console to facilitate the retaining of the cassette to the console and to at least partially assist in properly seating the cassette in the portion of the console meant to receive the cassette. As illustrated in FIG. 3, a cassette may include at least three sets of detents capable of accepting an attachment means provide by the console, such as, for example, upper detents 310, center detents 311, and lower detents 312. As will be described in greater detail below, the detents may be operated on in tandem or in a piecemeal fashion by a retention device of the surgical console.

An exemplary cassette may also include at least one pressurized fluid inlet 321 which may be in fluid communication with at least one filter within filter cavity 320. The pressurized fluid, for example, air, may be supplied to the cassette through fluid inlet 321 and introduced into pressurized irrigation tank 340 and may be in further communication with pressure sensor 360. There may similarly be at least one vacuum inlet 323 which may be in fluid communication with at least one filter within filter cavity 323. The vacuum applied through vacuum inlet 323 may be in communication with vacuum tank 342 and may be in further communication with aspiration channel 330 and aspiration channel 370. Each of the pressurized irrigation tank 340 and vacuum tank 342 may include a level sensing device 344 and 346, respectively.

Irrigation fluid may enter the cassette through inlet 382 and may enter irrigation channel 332. Irrigation valve 350 controls the flow of irrigation fluid and may allow for gravity fed irrigation fluid to be supplied to irrigation outlet 380 from irrigation channel 332 or pressurized irrigation fluid from pressurized irrigation tank 340. In either instance, and even when irrigation valve 350 is in the "off" position relative to both irrigation fluid sources, the amount of pressure associated with the delivery of the irrigation fluid may be measured by irrigation sensor 360. Similarly, aspiration pressure may be measured by the aspiration sensor 362 in close proximity to aspiration inlet 384. Aspiration fluid which may enter though aspiration inlet 384 may enter aspiration channel 330 under pressure produced by at least one peristaltic pump, for example, and may also enter vacuum tank 342 under the influence of at least a partial vacuum through valve 352.

Figure 4:
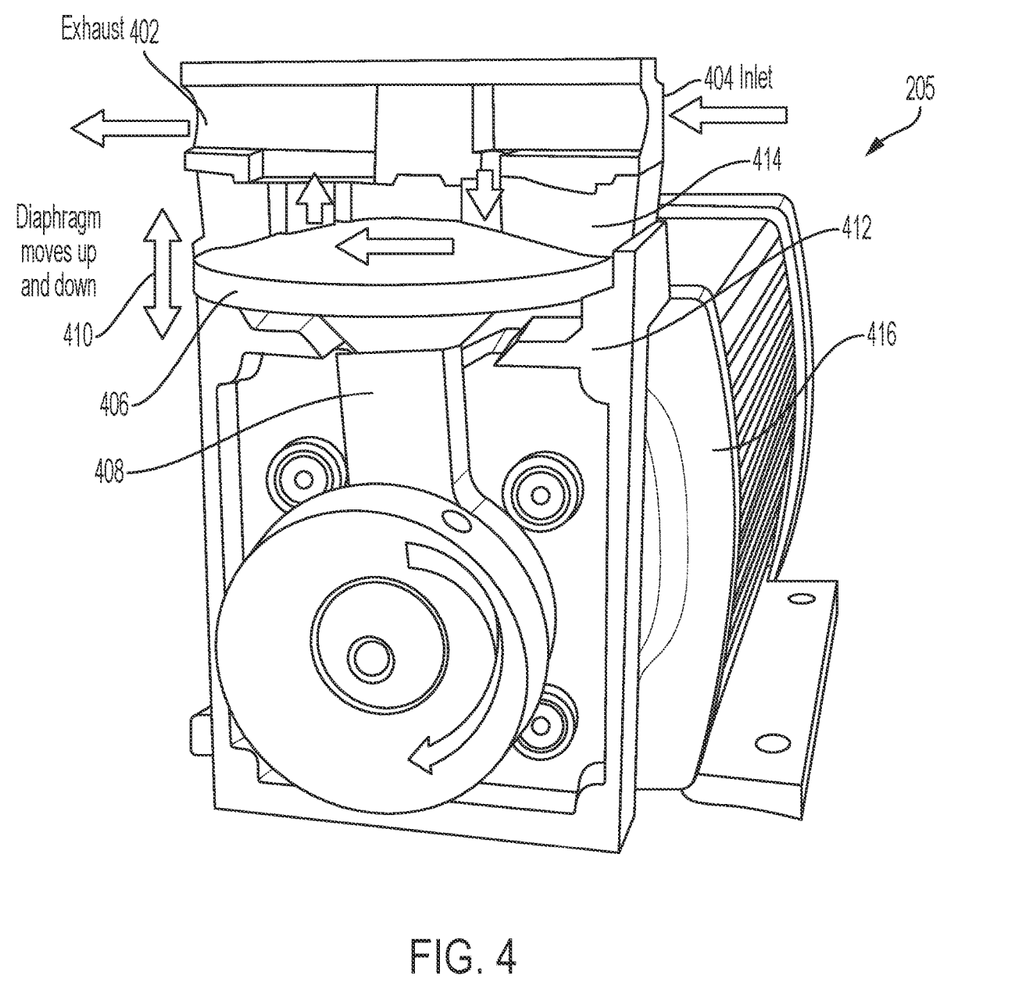
FIG. 4 illustrates an exemplary dual function pump and drive mechanism in accordance with at least one disclosed embodiment.

As illustrated in FIG. 4, an exemplary pressure and vacuum pump 205 is shown. A dual function pump used in conjunction with the phacoemulsification surgical system provides the generation of vacuum and pressure simultaneously. The exemplary pump shown may provide a dual-headed brushless diaphragm pump. The pump may include an inlet 404 and an exhaust 402. In an embodiment, inlet 404 may be coupled with an inlet valve and exhaust 402 may be coupled with an exhaust valve. Diaphragm 406 may move in an up and down motion (410). In an embodiment, diaphragm 406 may include at least two diaphragm pump heads (see for example FIG. 5A, pressure pump head 503 and vacuum pump head 505) above a diaphragm pump housing 412. In other embodiments, diaphragm 406 may include more than two diaphragm pump heads, e.g. three, four or more. In a preferred embodiment, diaphragm 406 pump includes two pump heads and the pump heads are double headed diaphragm pump heads. In another embodiment, one or more pump heads is a double headed diaphragm pump head. The pump housing may cause a connecting rod 408 to oscillate therefore causing the diaphragm to move up and down (410). On a downward stroke, the diaphragm would draw air into the inlet. On an upward stroke, air would be forced out via an outlet. The diaphragm may hermetically seal a compression chamber 414 of a drive mechanism 416.

A benefit of the dual function pump is the pump transfers, evacuates, and compresses air without the need of oil. Further benefits of the brushless pump is that it has a longer life than a traditional brushed configuration. The pump may come with an electronic controller capability of speed control, reading tachometer voltage, soft start (remote on/off) and the generation of an error out signal.

A dual function pump as described herein reduces the number of required pumps from two to one due to its capability to produce high flow pressure and deep vacuum simultaneously. The diaphragm pump is considerably less noisy than other conventional pressure and vacuum pumps. This is achieved through the pump running slower and via lower power consumption. A dual function pump as described provides a significant performance margin for what is required of the system to enable the system to run at a lower duty cycle.

A single pump being utilized, as opposed to dedicated pressure and vacuum pumps, requires additional valving to shut on or off the vacuum/pressure when the respective function is needed or not needed. In one example, when the surgical system does not need pressure the pressure isolation valve may switch its output to atmosphere and when pressure is needed whether for vitrectomy, pressurized irrigation, or both, the valve will redirect pressure flow into a pressure reservoir.

Figure 5A:
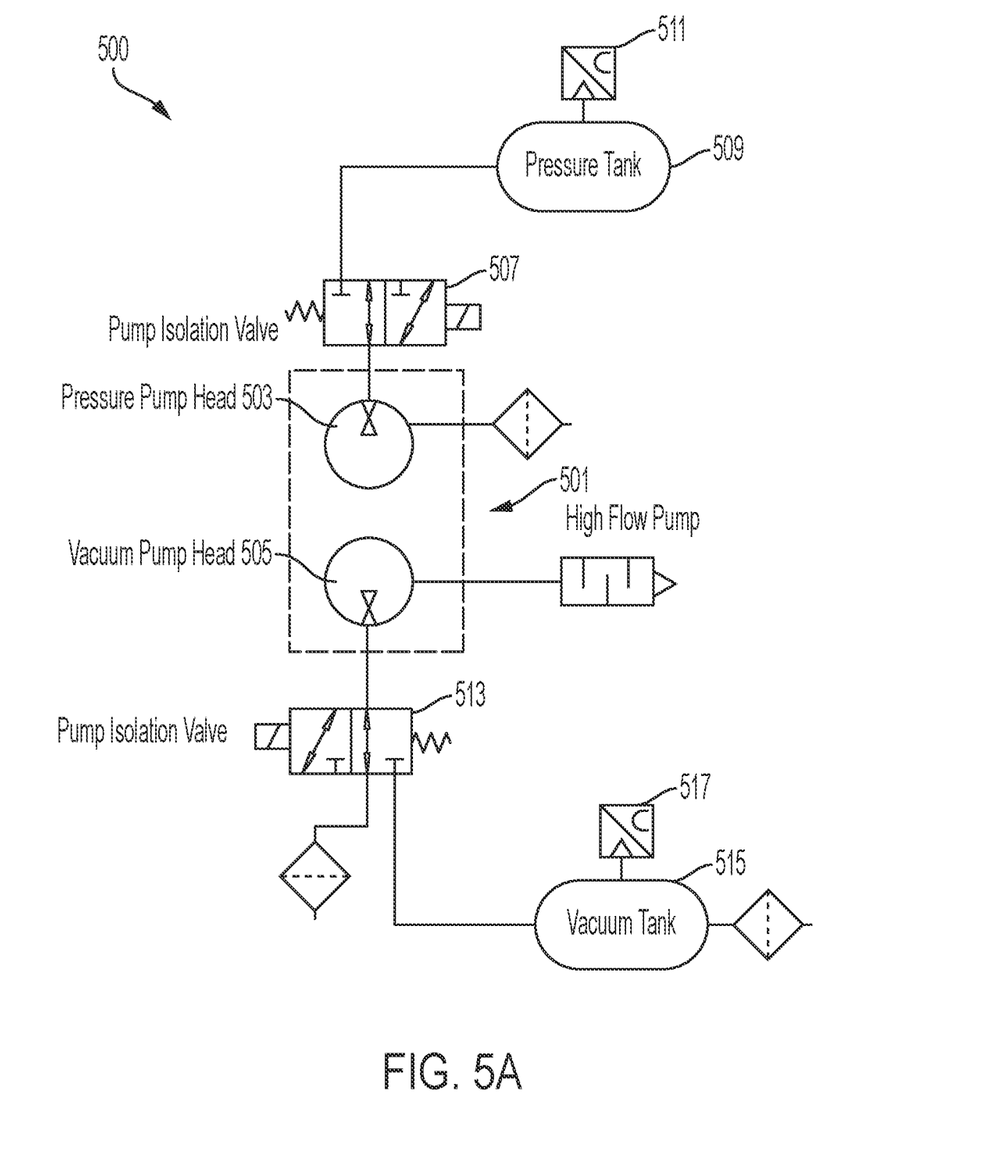
FIGS. 5A, 5B, and 5C are system level diagrams of an exemplary dual function pump and drive mechanism in accordance with at least one disclosed embodiment.

FIG. 5A is a diagram of an exemplary dual function pump system 500 having dual function pump/high flow pump 501. Dual function pump 501 includes a pressure pump head 503 and a vacuum pump head 505. In another embodiment, the dual function pump system 500 may also include a pump isolation valve 507 and a pressure tank 509 coupled with pressure pump head 503. Pressure tank 509 may be coupled with a transducer 511. Also, in an embodiment, dual function pump system 500 may also include a pump isolation valve 513 and vacuum tank 515 coupled with vacuum pump head 505. Vacuum tank 515 may be coupled with a transducer 517. The transducers 511 and 517 may be any transducer known in the art, e.g. a pressure transducer.

Figure 5B:
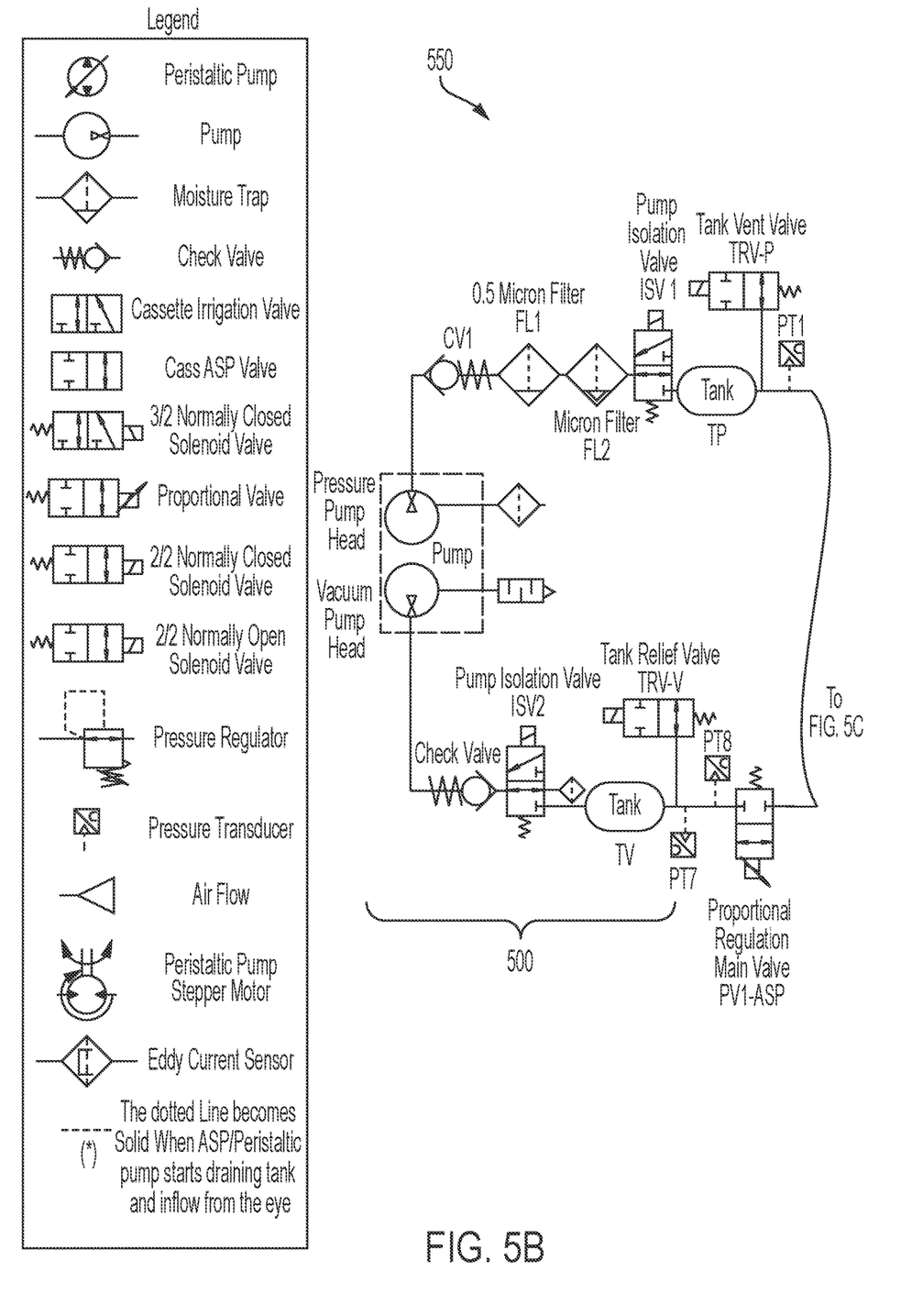
Figure 5C:
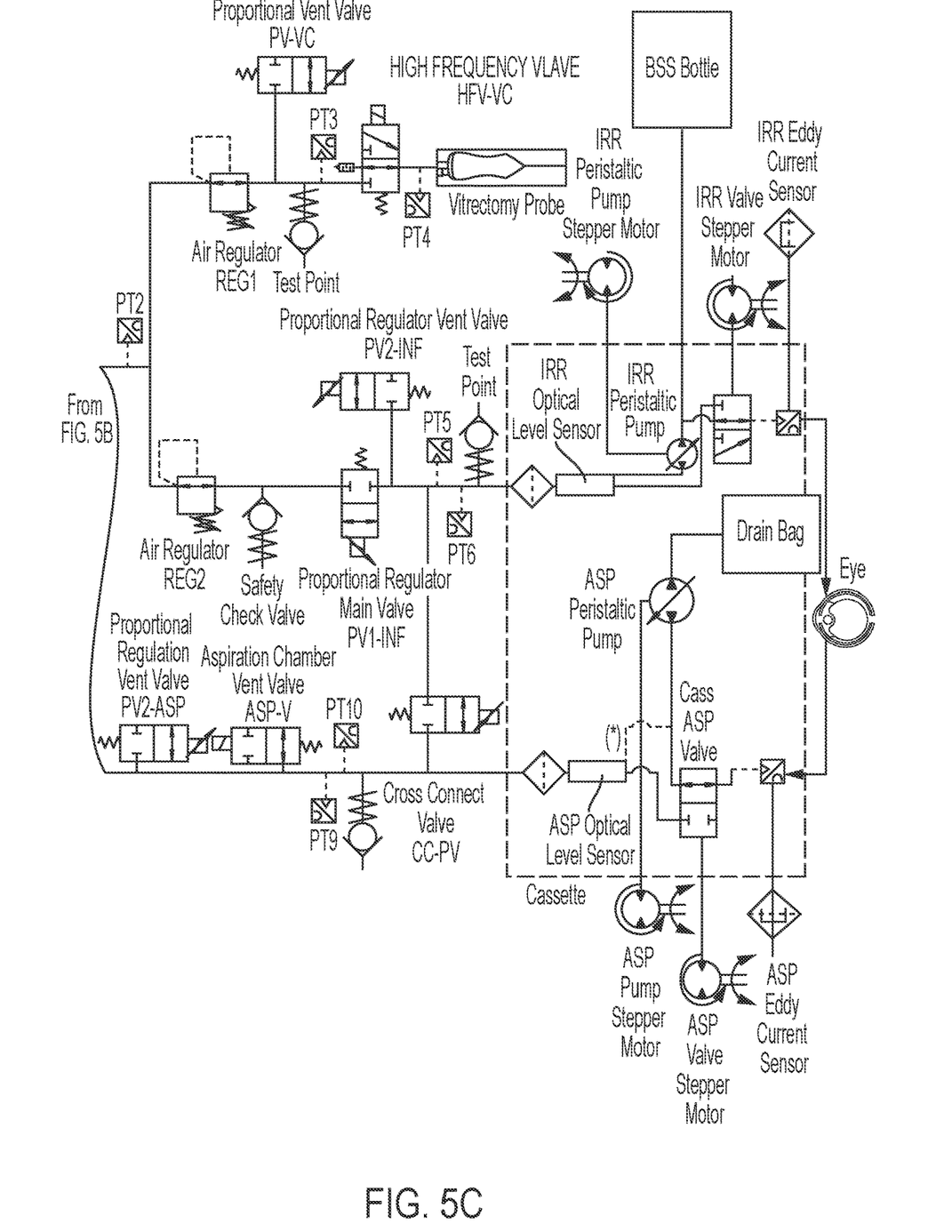

In an embodiment, dual function pump system 500 may be incorporated into a larger system 550 as shown in FIGS. 5B and 5C. Additional components such as isolation valves, tanks, check valves, filters, vent valves, and moisture traps may also be included into dual function system 500 or as shown in the larger system 550. The addition, removal and change in arrangement of components is also contemplated.

Those of skill in the art will appreciate that the herein described apparatuses, engines, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A system for distributing fluid in a phacoemulsification surgical system, comprising:
   a cassette adapted for single procedure use with a surgical console, the cassette comprising:
      a vacuum inlet;
      a pressure fluid inlet; and
      a set of channels configured for flow of fluid therethrough during a surgical procedure; and
   a dual function diaphragm pump configured to provide vacuum and pressure for movement of fluid within the set of channels, when the cassette is present in the surgical console during the surgical procedure;
   wherein the dual function diaphragm pump comprises:
      an inlet to provide vacuum to the vacuum inlet of the cassette;
      an exhaust to provide positive pressure to the pressure fluid inlet of the cassette;
      at least two diaphragm pump heads; and
      a connecting rod coupled at a first end to a surgical console pump motor and having an opposing end coupled to the at least two diaphragm pump heads and configured to oscillate via an electronic controller, causing diaphragms of the at least two diaphragm pump heads to move between respective first and second positions to selectively provide pressure and vacuum for fluid movement in the cassette.

2. The system of claim 1, wherein movement of the diaphragms between respective first and second positions causes air to be drawn into the inlet and forced out via the exhaust.

3. The system of claim 1, wherein the at least two diaphragm pump heads comprise a pressure pump head and a vacuum pump head.

4. The system of claim 1, wherein the dual function diaphragm pump provides a vacuum for fluid movement within the cassette.

5. The system of claim 1, wherein the dual function diaphragm pump provides a positive pressure for fluid movement within the cassette.

6. The system of claim 1, wherein the dual function diaphragm pump provides a positive pressure to fluid in a pressure reservoir within the cassette.

7. The system of claim 1, wherein the at least two diaphragm pump heads operate simultaneously.

8. The system of claim 1, wherein the dual function diaphragm pump comprises four diaphragm pump heads.

9. The system of claim 1, further comprising an inlet valve coupled with the inlet and an exhaust valve coupled with the exhaust.

10. A phacoemulsification surgical system, comprising:
a surgical console including a pump housing;
a surgical cassette configured to removably attach to the surgical console and interface with the pump housing when attached; the surgical cassette comprising:
  a vacuum inlet;
  a pressure fluid inlet; and
  a set of channels configured for flow of fluid through the surgical cassette; and
a dual function diaphragm pump configured to provide vacuum and pressure for movement of fluid through the set of channels of the surgical cassette when the surgical cassette is interfaced with the pump housing of the surgical console, the dual function diaphragm pump comprising:
  an inlet to provide vacuum to the vacuum inlet of the surgical cassette;
  an exhaust to provide positive pressure to the pressure fluid inlet of the cassette;
  at least two diaphragm pump heads; and
  a connecting rod coupled at a first end to the pump housing of the surgical console and coupled at an opposing end, to the at least two diaphragm pump heads and configured to oscillate via an electronic controller, causing diaphragms of the at least two diaphragm pump heads to move between respective first and second positions to selectively provide pressure and vacuum for the flow of fluid in the surgical cassette.

11. The phacoemulsification surgical system of claim 10, wherein the at least two diaphragm pump heads comprise a pressure pump head and a vacuum pump head.

12. The system of claim 1, wherein the cassette further comprises:
  a pressurized irrigation tank in fluid communication with the pressure fluid inlet;
  an irrigation fluid outlet;
  an irrigation valve disposed between the pressurized irrigation tank and the irrigation fluid outlet;
  a vacuum tank in fluid communication with the vacuum inlet;
  an aspiration inlet; and
  an aspiration pressure valve disposed between the vacuum tank and the aspiration inlet.

* * * * *